United States Patent
Olivo et al.

(10) Patent No.: US 11,635,327 B2
(45) Date of Patent: Apr. 25, 2023

(54) OPTICAL PROBE, RAMAN SPECTROSCOPY SYSTEM, AND METHOD OF USING THE SAME

(71) Applicant: Agency for Science, Technology and Research, Singapore (SG)

(72) Inventors: Malini Olivo, Singapore (SG); Gurpreet Singh, Singapore (SG); Renzhe Bi, Singapore (SG); Kapil Dev, Singapore (SG); Dinish Unnimadhava Kurup Soudamini Amma, Singapore (SG); Chris Jun Hui Ho, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 139 days.

(21) Appl. No.: 16/499,601

(22) PCT Filed: Mar. 29, 2018

(86) PCT No.: PCT/SG2018/050166
§ 371 (c)(1),
(2) Date: Sep. 30, 2019

(87) PCT Pub. No.: WO2018/182537
PCT Pub. Date: Oct. 4, 2018

(65) Prior Publication Data
US 2020/0103276 A1     Apr. 2, 2020

(30) Foreign Application Priority Data
Mar. 30, 2017   (SG) ............... 10201702588T

(51) Int. Cl.
*G01J 3/02*  (2006.01)
*G01J 3/44*  (2006.01)
*G01N 21/65* (2006.01)

(52) U.S. Cl.
CPC ............ *G01J 3/0218* (2013.01); *G01J 3/44* (2013.01); *G01N 21/65* (2013.01); *G01N 2201/08* (2013.01)

(58) Field of Classification Search
CPC .... A61B 5/0075; G01J 3/0218; G01J 3/0237; G01J 3/0272; G01J 3/44; G01N 21/65; G01N 2201/08
(Continued)

(56) References Cited

U.S. PATENT DOCUMENTS 3,778,643 A * 12/1973 Jaffe ................ H03H 7/345
                                                    327/277
5,983,125 A * 11/1999 Alfano ............... A61B 5/0075
                                                    600/473
(Continued)

FOREIGN PATENT DOCUMENTS

CN    102608076 A    7/2012
CN    103743718 A    4/2014
(Continued)

OTHER PUBLICATIONS

International Search Report for International Application No. PCT/SG2018/050166 dated Jun. 12, 2018, pp. 1-4.
(Continued)

*Primary Examiner* — Sunghee Y Gray
(74) *Attorney, Agent, or Firm* — Shackelford, Bowen, McKinley & Norton, LLP

(57) ABSTRACT

Provided is an optical probe, and a Raman spectroscopy system using such, including excitation and detection optics coupled to a sampling optics via a beam splitter, in confocal arrangement with a sample focal plane of the sampling optics. The detection optics is arranged to receive Raman signal from the sample focal plane and direct it onto a tip of a detection optical fiber. The optical probe may further
(Continued)

include a positioning device mechanically coupled to the sampling optics and configured to control a position of the sample focal plane. In the Raman spectroscopy system a light source is coupled to the excitation optics via an excitation optical fiber, and a spectrometer is coupled to a detection optics via a detection optical fiber. Provided is further a method for measuring Raman signal depth profile in a sample, wherein sample's Raman spectra is measured and stored at different focal plane positions.

19 Claims, 8 Drawing Sheets

(58) Field of Classification Search
USPC .......................................................... 356/301
See application file for complete search history.

(56) References Cited

U.S. PATENT DOCUMENTS

| | | | |
|---|---|---|---|
| 6,263,233 B1 | 7/2001 | Zavislan et al. | |
| 6,310,686 B1 | 10/2001 | Jiang | |
| 6,681,133 B2 | 1/2004 | Chaiken et al. | |
| 7,148,963 B2 | 12/2006 | Owen et al. | |
| 2005/0099676 A1* | 5/2005 | Tokura | H04B 10/2916 359/349 |
| 2005/0248759 A1 | 11/2005 | Wang et al. | |
| 2006/0063991 A1* | 3/2006 | Yu | G01N 21/65 600/322 |
| 2008/0014654 A1* | 1/2008 | Weisman | G01N 21/645 436/172 |
| 2009/0021724 A1* | 1/2009 | Mahadevan-Jansen | A61B 5/445 356/73 |
| 2010/0214562 A1 | 8/2010 | Mahadevan-Jansen et al. | |
| 2010/0245816 A1 | 11/2010 | Shen et al. | |
| 2011/0081111 A1 | 4/2011 | Li et al. | |
| 2012/0176613 A1 | 7/2012 | Marple et al. | |
| 2012/0314206 A1 | 12/2012 | Spizig et al. | |
| 2013/0083322 A1* | 4/2013 | Iketaki | G01N 21/65 356/301 |
| 2014/0340677 A1 | 11/2014 | Sataka et al. | |
| 2015/0276480 A1* | 10/2015 | Ghosh | G01N 21/65 356/301 |
| 2016/0270666 A1* | 9/2016 | Vermeulen | A61B 1/063 |
| 2017/0184453 A1* | 6/2017 | Wang | G01J 3/44 |
| 2017/0234796 A1* | 8/2017 | Kuster | A61B 1/0646 359/350 |
| 2017/0235118 A1* | 8/2017 | Kuster | G02B 21/0012 600/476 |
| 2018/0328840 A1* | 11/2018 | Green | G01J 3/28 |

FOREIGN PATENT DOCUMENTS

| | | |
|---|---|---|
| DE | 102012216164 A1 | 3/2014 |
| WO | 2011072380 A1 | 6/2011 |
| WO | 2011083111 A1 | 7/2011 |

OTHER PUBLICATIONS

Written Opinion of the International Searching Authority for International Application No. PCT/SG2018/050166 dated Jun. 12, 2018, pp. 1-7.

Extended European Search Report for European Patent Application No. 18777757.8 dated Nov. 13, 2020, pp. 1-13.

Ann-Kathrin Kniggendorf, "Resonanz Raman Mikro-Spektroskopie zur Analyse Bakterieller Biofilme," Jun. 28, 2011, pp. 1-95.

McCain et al., "Multi-Excitation Raman Spectroscopy Technique for Fluorescence Rejection," Optics Express, vol. 16, No. 15, Jul. 21, 2008, pp. 1-17.

Brachtel et al., "Spectrally Encoded Confocal Microscopy (SECM) for Diagnosing of Breast Cancer in Excision and Margin Specimens," Laboratory Investigation, vol. 96, Jan. 18, 2016, pp. 459-467.

* cited by examiner

OPTICAL PROBE, RAMAN SPECTROSCOPY SYSTEM, AND METHOD OF USING THE SAME

CROSS-REFERENCE TO RELATED APPLICATION

This application claims the benefit of priority of Singapore application No. 10201702588T filed on Mar. 30, 2017, the contents of it being hereby incorporated by reference in its entirety for all purposes.

TECHNICAL FIELD

Various aspects of this disclosure relate to an optical probe for a Raman spectroscopy system. Various aspects of this disclosure relate to a Raman spectroscopy system using an optical probe as disclosed herein. Various aspects of this disclosure relate to a method for using a Raman spectroscopy system.

BACKGROUND

Raman scattering was predicted and observed in 1920s. Starting from 1960s, Raman spectroscopy became more and more popular because of the simplification of instrument and its high sensitivity. Since 1980s, fiber based Raman spectroscopy systems were developed. Then, confocal Raman system was introduced in 1990s. There are several companies who can provide handheld fiber based Raman probe. However, such handheld fiber based Raman probes are only able to provide a signal capture integrated over the whole illuminated area of the sample.

There is a need for improved Raman probes which are easier to be handheld.

SUMMARY

Various embodiments may provide an optical probe for Raman spectroscopy system. The optical probe may include an excitation optics. The optical probe may include a detection optics. The optical probe may include a sampling optics. The excitation optics and the detection optics may be optically coupled to the sampling optics via a beam splitter. The excitation optics and the detection optics may be in confocal arrangement with a sample focal plane of the sampling optics. The sampling optics and the detection optics may be arranged to receive a Raman signal from the sample focal plane and direct it onto a tip of a detection optical fiber.

Various embodiments may provide a Raman spectroscopy system. The Raman spectroscopy system may include a spectrometer. The spectrometer may include a sensor. The Raman spectroscopy system may include a light source. The Raman spectroscopy system may include an optical probe as further disclosed herein, for example, as summarized above. The light source may be configured to be optically coupled to a tip of an excitation optical fiber, wherein the tip is distal from the excitation optics. The spectrometer may be configured to be optically coupled to a tip of the detection optical fiber which is distal from the detection optics.

Various embodiments may provide a method for measuring Raman signal depth profile in a sample. The method may be carried out with a Raman spectroscopy system as further disclosed herein, for example, as summarized above. The Raman spectroscopy system may comprise a spectrometer, an optical probe as disclosed herein, and a positioning device mechanically coupled to the sampling optics and configured to control a position of the sample focal plane. The method may include the step of (i) driving the positioning device thereby controlling the position of the sample focal plane to a first position. The method may include the step of (ii) measuring a Raman signal. The method may include the step of (iii) recording at least one of a Raman signal or a processed information obtained from processing the Raman signal, at the first position. Step (iii) may further include storing an associated data record containing an information in respect to the first position. The method may include repeating steps (i), (ii), and (iii) for a second and optionally further position, instead of the first position. Each of the first, second and optionally further position may be different from each other.

BRIEF DESCRIPTION OF THE DRAWINGS

The invention will be better understood with reference to the detailed description when considered in conjunction with the non-limiting examples and the accompanying drawings, in which.

DETAILED DESCRIPTION

Figure 1:
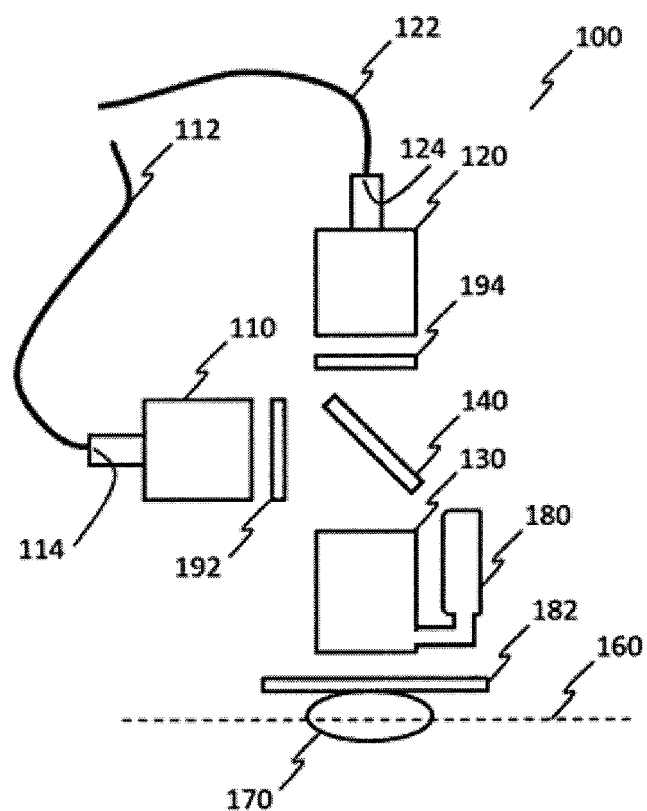
FIG. 1 shows a schematic illustration of an optical probe 100 for a Raman spectroscopy system according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Embodiments described in the context of one of the probes, methods or systems are analogously valid for the other probes, methods or systems. Similarly, embodiments described in the context of a probe are analogously valid for a system, and vice versa. Also embodiments described in the context of a probe are analogously valid for a method, and vice versa. Further, embodiments described in the context of a system are analogously valid for a method, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of the present disclosure and also according to various embodiments, the articles "a", "an" and "the" as used with regard to a feature or element include a reference to one or more of the features or elements.

In the context of the present disclosure and also according to various embodiments, the term "about" or "approximately" as applied to a numeric value encompasses the exact value and a reasonable variance.

As used herein, the term "and/or" includes any and all combinations of one or more of the associated listed items. For example "A and/or B" is identical to "A, or B, or A and B".

The optical probe of the present disclosure provides a handheld probe that enables confocal Raman measurement, which may be used for clinical or other applications. One possible application for the optical probe is measurement on biological tissue; such as skin samples that have been extracted, for example from the human or animal body. Another possible application for the optical probe is measurement in vivo, for example on skin tissue. It was surprisingly found that the Raman spectroscopy system disclosed herein can provide the same level of depth resolution and sensitivity as a free space confocal Raman system, with all the advantages of being small enough to be held on and be operated by hand.

Illustratively, the present disclosure provides the first fiber based optical probe for a Raman spectroscopy system which is able to measure a depth profile of a sample.

Confocal is achieved by a pinhole approach, wherein a detection optical fiber may be used in place of a pinhole, and use of detection optics to focus a Raman signal onto the tip of the detection optical fiber. An example of the detection optics is an integrated collimator. Accordingly, in various embodiments, the detection optics may be configured to focus the Raman signal onto the tip of the detection optical fiber. Also, the detection optics and the detection optical fiber may be arranged in relation to each other such that Raman signal is focused onto the tip of the detection optical fiber. The detection optics and the detection optical fiber may be arranged in relation to each other such that out of focus Raman signal is not optically coupled into the detection optical fiber.

In the context of the present disclosure and also according to various embodiments, the term "couple" (or its derivate "coupleable" and "coupled") may refer to optically couple (or its derivate "optically coupleable" and "optically coupled"). For example, the detection optics and the detection optical fiber may be arranged in such a position that the tip of the detection optical fiber may receive Raman signal from the detection optics, such that Raman signal is coupled into the fiber. In this example, the detection optical fiber and the detection optics are optically coupled.

In the context of the present disclosure and also according to various embodiments, an optical probe for Raman spectroscopy system is provided. The term "optical probe" may refer to a probe which is coupleable with a remaining part of a Raman spectroscopy system, for example optically coupleable with a spectrometer and optically coupleable with a light source. The optical probe may be optically coupleable via optical fibers, for example an excitation optical fiber and a detection optical fiber. The optical probe may be handheld. The term "handheld" may refer to able to be held by a hand of an operator, for example not fixed to a heavier structure, for example with overall weight of less than 1 kg, for example less than 500 g.

The optical probe comprises an excitation optics and a detection optics optically coupled to a sampling optics. In the context of the present disclosure and also according to various embodiments, the term "optics" (for example, as in "excitation optics", "detection optics", "sampling optics") may refer to an arrangement of, and including, optical components. The arrangement may further include mechanical components used for supporting the optical components. The arrangement may further include one or more connectors, for example optical fiber connector(s). The optical components may include one or more lenses, and/or one or more optical filters.

The excitation optics may be configured to receive an excitation optical fiber, wherein the excitation optical fiber is an optical fiber configured to transmit excitation light from a light source. The term "excitation optics" may refer to the optics used for providing excitation, for example to direct the excitation light from the tip of the excitation optical fiber onto the sampling optics. In various embodiments, the tip of the excitation optical fiber is positioned at the focus of the excitation optics.

In addition to the excitation optics, the optical probe may also comprise a detection optics. The detection optics may be configured to receive a detection optical fiber, wherein the detection optical fiber is an optical fiber configured to transmit Raman signal. The term "detection optics" may refer to the optics used for the Raman signal, for example to direct the Raman signal, from the sampling optics to the tip of the detection optical fiber.

The excitation optics and the detection optics are optically coupled to a sampling optics. The term "sampling optics" may refer to the optics used close to the sample, which may provide the sample focal plane. The excitation optics and the detection optics may be optically coupled to the sampling optics via a beam splitter, and may be in confocal arrangement with the sample focal plane of the sampling optics. The sampling optics may be an optics which is common for the excitation optics and the detection optics. One example of a sampling optics is an objective lens. The sampling optics and the detection optics may be arranged to receive a Raman signal from the sample focal plane and direct it onto a tip of a detection optical fiber.

The excitation optics and the sampling optics may be arranged to direct light from the excitation optical fiber onto the sample focal plane. The excitation light may be directed from the excitation optics to the sample via the sampling optics. The Raman signal may be collected by the sampling optics and directed to the detection optics. The optical path may be divided by a beam splitter, such that the optical path between the beam splitter and the sample focal plane may be essentially the same for the excitation light and the Raman signal. One example of a beam splitter is a dichroic mirror.

According to various embodiments, a filter may be arranged between the beam splitter and the detection optics. Alternatively, the detection optics may include a filter. In this context, the filter may be for example a notch filter, to eliminate excitation light, and to enable the Stokes and/or anti-Stokes part of the Raman signal to pass.

In the context of the present disclosure and also according to various embodiments, the excitation light may be coherent light, for example from laser light. The light source is configured to provide excitation light, for example a laser. The light may be at least partially coherent, for example it may be a coherent light, for example laser light. Consequently the light source may be a source of at least partially coherent light, for example coherent light. The excitation light may be essentially monochromatic, for example, the excitation light may be a laser at a specific laser wavelength. Further optical means, such as optical filters may be used to narrow the wavelength bandwidth of the excitation light. Alternatively or in addition, said optical filters may be configured to clean the fluorescence signal from the excitation optical fiber. For example a band pass filter may be configured to block at least a substantial part of the fluorescence from the fiber while allowing the excitation light to be transmitted. The main wavelength of the excitation light may range, for example, from the ultra violet to the near infra-red. The main wavelength of the excitation light may range, for example, from 220 nm to 1100 nm.

When Raman laser excitation source goes through optical fiber 112, the laser stimulates Raman signal from optical fiber 112, which may contribute to noise within the Raman signal generated from sample 170. Thus, bandpass filter 192 is used to only allow the Raman laser excitation source to pass through while blocking the Raman signal generated from optical fiber 112. Dichroic mirror 140 reflects the Raman laser excitation source at right angles into the sample, while allowing the Raman signal generated from sample 170 which is at a longer wavelength compared to the excitation to pass through into the detector. Notch filter 194 blocks the Raman laser excitation source from passing through into the detector. All these ensure that only the Raman signal generated from sample 170 and nothing else reaches the detector.

In the context of the present disclosure and also according to various embodiments, the term "optical fiber" in the singular form (as in excitation optical fiber or detection optical fiber) may refer to a single optical fiber, and may exclude a fiber bundle. Each of the excitation optical fiber and the detection optical fiber may be selected to be able to transmit excitation light of essentially the same wavelength, for example of the wavelength of the excitation light. That is because the Raman signal (Stokes or anti-Stokes) is shifted from the excitation light only by a few nanometers.

In various embodiments, the excitation optics comprises a collimator. In some embodiments, the excitation optics comprises a first collimator, while the detection optics comprises a second collimator. In the context of the present disclosure and also according to various embodiments, the first collimator and the second collimator may be identical and therefore interchangeable. That enhances the symmetry of the optical probe and facilitates calibration.

The optical probe disclosed herein may further comprise a positioning device mechanically coupled to the sampling optics and configured to control a position of the sample focal plane. In the context of the present disclosure and also according to various embodiments, the term "positioning device" may refer to mechanical device to provide position displacement in reaction to an electrical signal, for example, to control a position of the sample focal plane. A positioning device may be, for example, an electrical motor, such as, e.g., a micromotor. The control of the position of the sample focal plane allows for depth sectioning of sample measurements. In one example, the positioning device may be a motorized stepper.

In a second aspect, a Raman spectroscopy system is provided. In the context of the present disclosure and also according to various embodiments, the term "spectroscopy system" may be implemented as a spectroscopy apparatus.

The Raman spectroscopy system may comprise a spectrometer comprising a sensor, a light source, and an optical probe disclosed herein. The light source may be configured to be optically coupled to a tip of an excitation optical fiber which is distal from the excitation optics, and the spectrometer may be configured to be optically coupled to a tip of the detection optical fiber which is distal from the detection optics.

The spectroscopy system according to various embodiments, may include a computation unit. Alternatively or in addition, spectroscopy system according to various embodiments may be connectable to a personal computation device (for example a personal computer). The personal computation device may be configured, for example, for at least one of: controlling the spectroscopy system, data manipulation, data presentation, a combination of the foregoing.

The figures are of schematic nature, the proportion and scale may have been modified to improve the visibility and to easier explain the invention.

FIG. 1 shows a schematic illustration of an optical probe 100 for a Raman spectroscopy system according to various embodiments. FIG. 1 also shows a sample 170. Shown in the figure is an optical probe 100 including an excitation optics 110 and a detection optics 120 which may be optically coupled to the sampling optics 130, as shown in the figure by means of example, via a beam splitter 140. The beam splitter may be, e.g. a dichroic mirror. The dichroic mirror may be configured to reflect the excitation light, e.g. the laser light, from the excitation optics to the sampling optics. The dichroic mirror may be further configured to allow transmission of the Raman signal from the sampling optics to the detection optics, for example by allowing only those wavelengths longer than the excitation light (e.g. laser) to pass. FIG. 1 also shows a positioning device 180 which is connected to the sampling optics 130, and is able to control the positioning of the sampling optics of 130, such as the z-position of sampling optics 130 in order to adjust the focal plane. 182 is a glass slide. In various embodiments, the positioning device may be mechanically coupled on one side (an example of one side of the positioning device is a motor housing of the motor) to the sampling optics. The mechanical coupling may be directly, or indirectly, for example via another mechanical structure of the optical probe, for example a housing. The optical probe 100 may be arranged such that the image from the tip 114 of the excitation optical fiber 122 is projected with focus on the sample focal plane 160. And an image of the sample focal plane 160, for example, carrying the Raman signal, is projected onto the tip 124 of a detection fiber optics 122, which tip 124 is positioned at a focal plane of the detection optics. Therefore, the optical probe is confocal. The handheld probe 100 may include a filter 192 for filtering the excitation light to a narrow part of the spectrum. The filter 192 may be positioned, e.g. between the beam splitter 140 and the excitation optics 110. The handheld probe 100 may include an additional filter 194 for filtering remains of the signals from the sample which are not Raman scattered by the sample, for example Rayleigh light. The additional filter could, e.g., cut out the wavelength of the excitation light, and allow only the Stokes or the anti-Stokes part of the Raman signal to be transmitted to the detection optics. The additional filter 194 may be positioned, e.g. between the beam splitter 140 and the detection optics 120.

According to various embodiments, a portable stand may be provided, which may be positioned on a flat surface, such as a table, and may be configured to receive the optical probe. An operator of the portable probe may rest the probe on the stand, thus not needing to hold the optical probe all the time. This may be provide rest for the operator, in particular for heavier probes.

Figure 2:
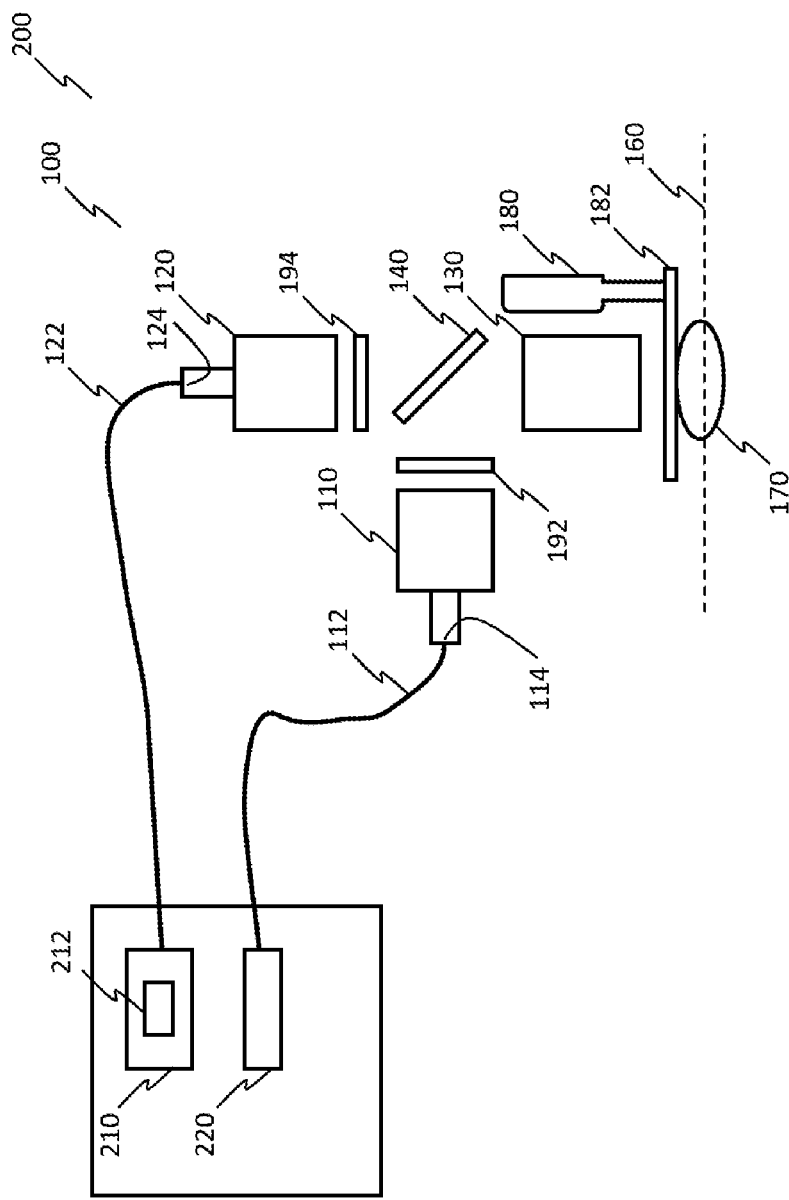
FIG. 2 shows a schematic illustration of a Raman spectroscopy system 200 including an optical probe 100 according to various embodiments.

FIG. 2 shows a schematic illustration of a Raman spectroscopy system 200 including an optical probe 100 according to various embodiments. The optical probe 100 is identical to the one in FIG. 1. The Raman spectroscopy system 200 may further include a spectrometer 210 and a light source 220. The light source 220 may be configured to emit the excitation light. The light source may be configured to be optically coupled to a tip of an excitation optical fiber 112 which is distal from the excitation optics 110. The spectrometer 210 may include a sensor 212 (as will be explained below), and is configured to be optically coupled to a tip of the detection optical fiber 122 which is distal from the detection optics 120.

In various embodiments, both the excitation fiber optics and the detection fiber optics may be at least partially protected inside a tube, which may for example be formed of plastics, thus forming a single cable. This may facilitate the usage of the optical probe by an operator, as he/she does not need to too careful with two optical fibers when handling the optical probe.

Figure 3:
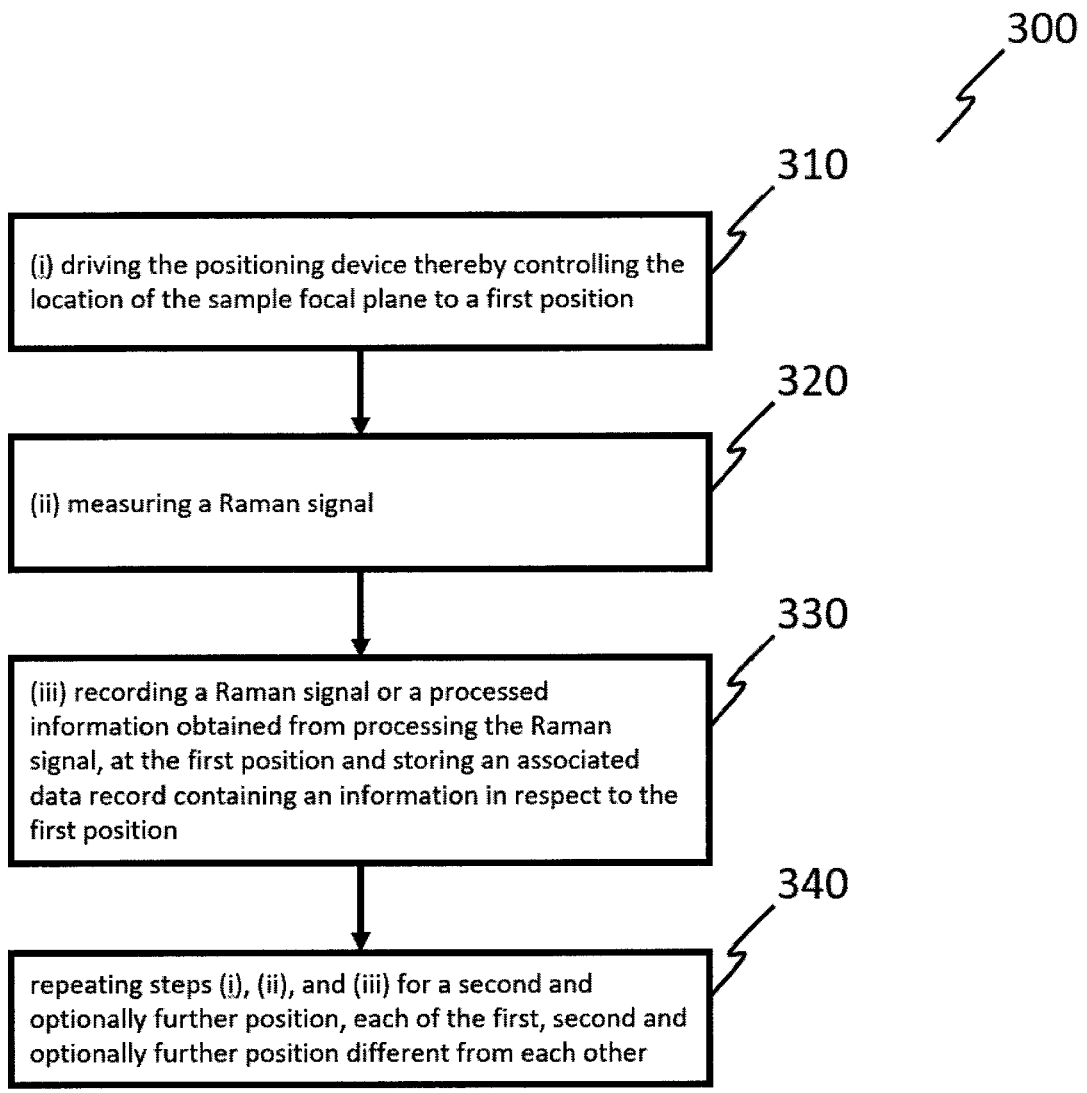
FIG. 3 shows a flowchart of a method 300 according to various embodiments, for measuring Raman signal depth profile in a sample.

FIG. 3 shows a flowchart of a method 300 for measuring Raman signal depth profile in a sample, according to various embodiments. The method may be carried out with a Raman spectroscopy system as disclosed herein, for example, the Raman spectroscopy system 200 described in connection with FIG. 1 and FIG. 2. Further, to carry out the method, a computation unit and/or a personal computation device may be utilized, for example for processing signal and/or storing data. The method 300 may include the step 310 of (i) driving the positioning device thereby controlling the position of the sample focal plane to a first position. The method 300 may include the step 320 of (ii) measuring a Raman signal. The method 300 may include the step 330 of (iii) recording at least one of a Raman signal or a processed information obtained from processing the Raman signal, at the first position. The step 330 of (iii) may further include storing an associated data record containing an information in respect to the first position. The method 300 may include the step 340 of repeating steps 310, 320, 330 ((i) to (iii)) for a second and optionally further position instead of the first position. Each of the first, second and optionally further position may be different from each other. Thus a depth profile may be generated by recording a set of data points, each data point including at least one of a Raman signal or a processed information obtained from processing the Raman signal and an associated data record containing an information in respect to the position.

Though not depicted in FIG. 3, the method for measuring Raman signal depth profile in a sample may further comprise: for a same position, carrying out steps (ii) and (iii) for an excitation light at a first wavelength and carrying out steps (ii) and (iii) again for the excitation light at a second wavelength; and wherein the method further optionally comprises determining a difference of the Raman signals or of the processed information obtained from processing the Raman signals obtained for the first wavelength and for the second wavelength. In so doing, background from two overlapping fluorescence spectrum may be subtracted for measuring Raman signal depth profile in the sample.

Alternatively, or in addition to the above, the method may further optionally comprise adjusting a difference of the Raman signals or of the processed information obtained from processing the Raman signals obtained for the first wavelength and for the second wavelength using an excitation light which is tunable to match an order of a spectral width of the Raman signals from one of more components of interest in the sample, such as a skin sample. Advantageously, this allows a tunable laser excitation wavelength gap based on shifted excitation Raman difference spectroscopy (SERDS) effect (as will be described herein later) to accommodate for various components of interest in a sample with different spectral widths of Raman signals for measuring Raman signal depth profile in the sample, and which may in turn provide for higher signal-to-noise ratios for the measurement.

The method may further comprise calibrating the position of the excitation optics and the position of the detection optics before performing a Raman signal measurement. In various embodiments, the method may further comprise acquiring a calibration depth profile Raman signal with a calibration sample and generating a calibration position data set. The calibration data set may be used in the method disclosed herein for calculating the position in a unit of distance, wherein the position is a relative position from a reference position of a sample.

According to various embodiments, the method for measuring Raman signal may include a step of determining the organic molecules for which signal is provided in the measured Raman signal. Such step may be carried out, for example, by an un-mixing algorithm. Thus, the Raman spectroscopy system and the method may provide information of different molecules at different depth.

FIGS. 4A to 6 show examples according to various embodiments of the present disclosure.

Figure 4A:
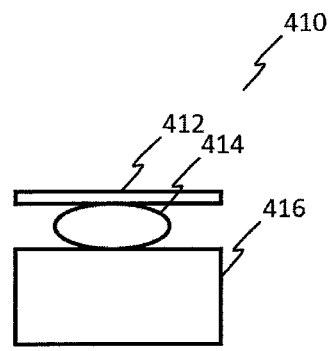
FIG. 4A shows a schematic illustration of a sample 410 with a liquid 414 on a support 416, wherein the liquid is covered by a glass cover 412.
Figure 4B:
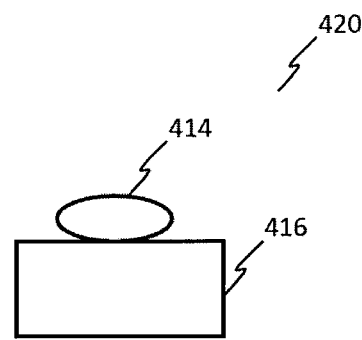
FIG. 4B shows a schematic illustration of a sample 420 similar to the sample 410 of FIG. 4A, except that the liquid is not covered by a glass cover.

FIG. 4A shows a schematic illustration of a sample 410 with a liquid 414 on a glass support 416, wherein the liquid is covered by a glass cover 412. The liquid 414 is linoleic acid. FIG. 4B shows a schematic illustration of a sample 420 identical to the sample 410 of FIG. 4A, except that the liquid is not covered by a glass cover. The samples 410 and 420 are used in examples of measurements taken with a Raman spectroscopy system and an optical probe, in accordance to various embodiments. The optical probe is held in proximity to the sample for example, via a clamping support, preferably with a motorized stage for moving in small step sizes to exert different levels of pressure on the sample, the position of the focal plane is adjusted to a first position corresponding to the glass cover 412 and a first Raman signal is measured. The position of the focal plane is adjusted to a second position corresponding to the liquid 414 and a second Raman signal is measured.

Figure 5:
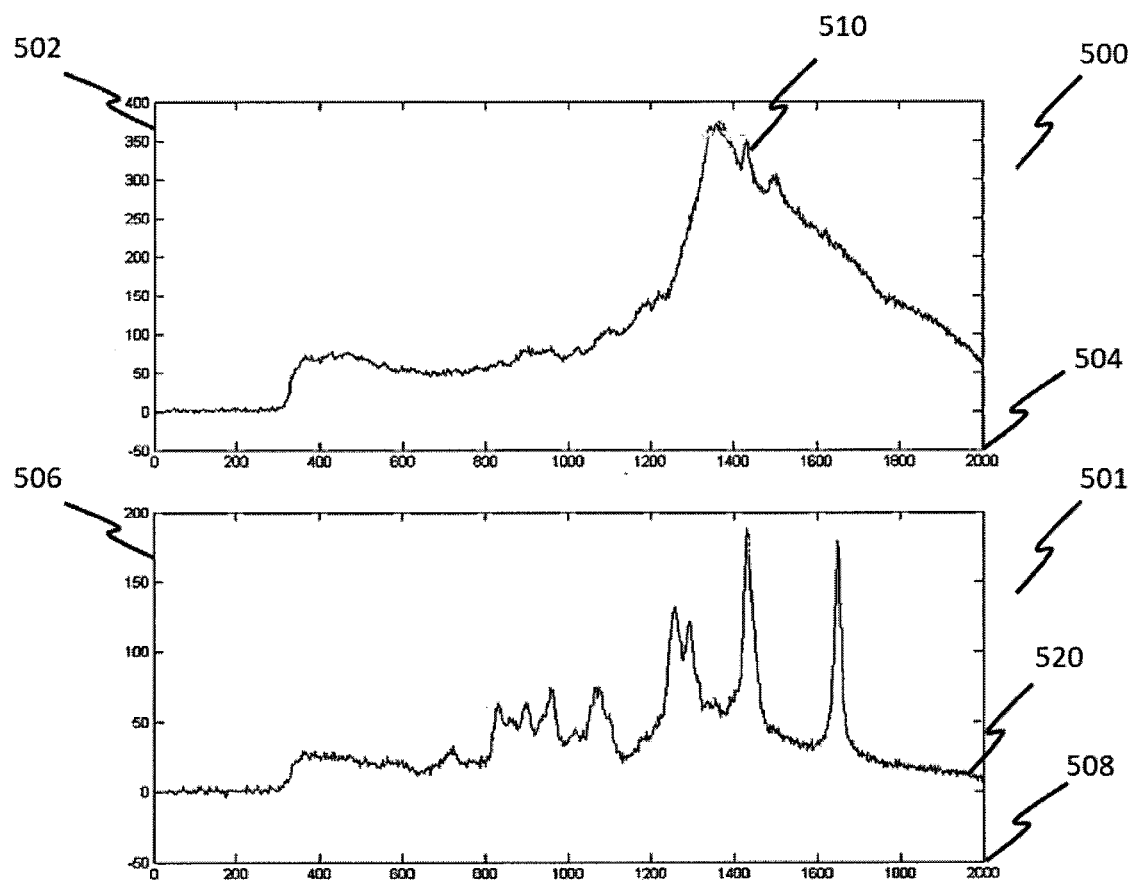
FIG. 5 shows a Raman spectrum 510 measured on sample 410 at a first position, and a Raman spectrum 520 measured on sample 410 at a second position.

FIG. 5 shows a plot 500 with horizontal axis 504 in wavelength ($cm^{-1}$) and vertical axis 502 in arbitrary intensity, with a Raman spectrum 510 corresponding to the first measured Raman signal measured on the sample 410 at the first position. FIG. 5 further shows a plot 501 with horizontal axis 508 in wavelength ($cm^{-1}$) and vertical axis 506 in arbitrary intensity, with a Raman spectrum 520 corresponding to the second measured Raman signal measured on sample 410 at the second position. As can be seen, with the measurements taken with an optical probe according to various embodiments, it is possible to clearly discern the Raman spectra of glass (510) and linoleic acid (520).

According to various embodiments, the optical probe allows for a selective confocal depth Raman measurement of a sample. The depth resolution may be determined by the numerical aperture (NA) of the sampling optics and the detection optical fiber core size. Bigger NA and smaller detection optical fiber core size will result in higher depth resolution. The excitation optical fiber and the detection optical fiber may be of same core size.

According to various embodiments, an automatic depth Raman measurement depth profile may be measured on a sample, for example by using the positioning device, e.g. a motorized stepper.

In an exemplary measurement of sample 420, the optical probe is held in proximity [to the sample, the position of the focal plane is adjusted to a first position corresponding to the liquid 414 and a third Raman signal is measured. The position of the focal plane is adjusted to a second position corresponding to the liquid glass support 416 and a fourth Raman signal is measured.

Figure 6:
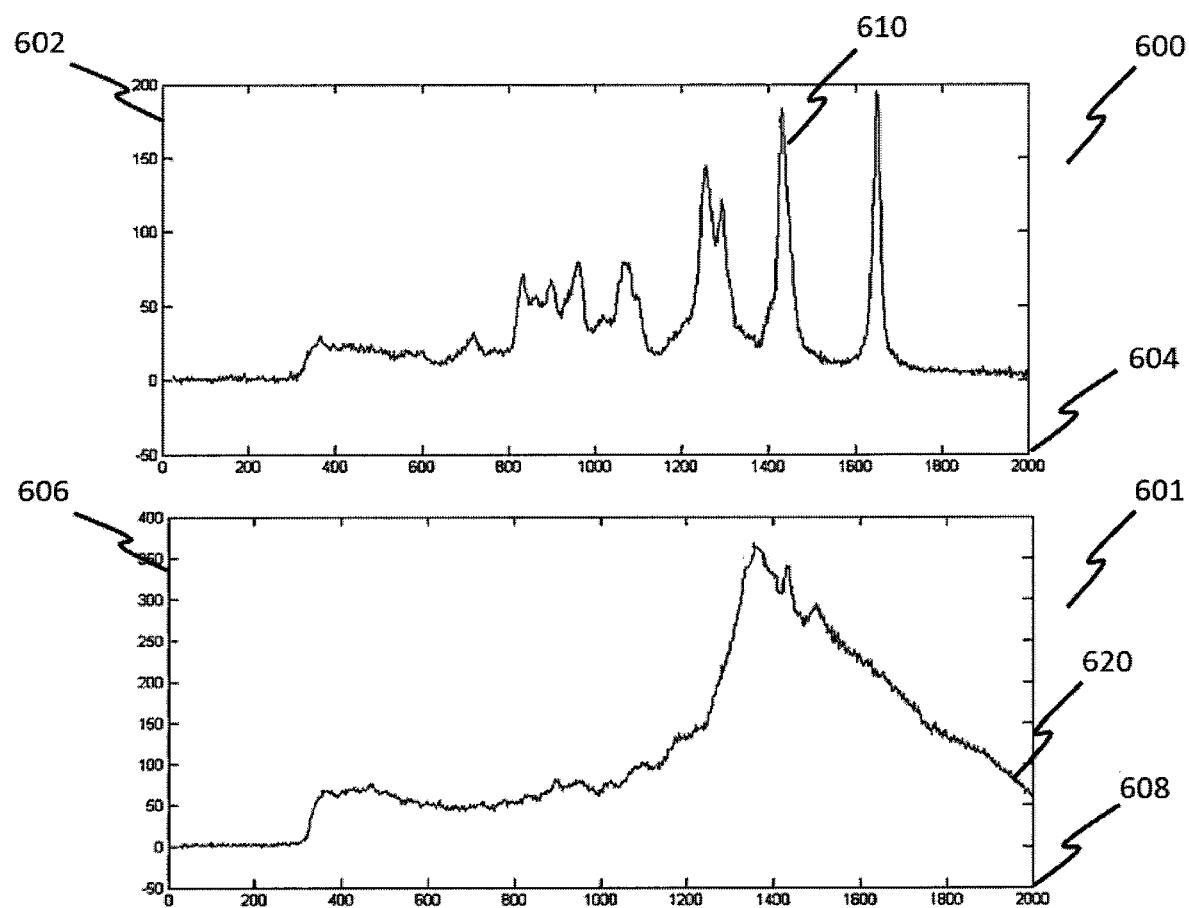
FIG. 6 shows a Raman spectrum 610 measured on sample 420 at a first position, and a Raman spectrum 620 measured on sample 420 at a second position.

FIG. 6 shows a plot 600 with horizontal axis 604 in wavelength (cm$^{-1}$) and vertical axis 602 in arbitrary intensity, with a Raman spectrum 610 corresponding to the third measured Raman signal measured on the sample 420 at the first position. FIG. 6 further shows a plot 601 with horizontal axis 608 in wavelength (cm$^{-1}$) and vertical axis 606 in arbitrary intensity, with a Raman spectrum 620 corresponding to the fourth measured Raman signal measured on sample 420 at the second position. As can be seen, with the measurements taken with an optical probe according to various embodiments, it is possible to clearly discern the Raman spectra of linoleic acid (610) and glass (620).

In another example, surface enhanced Raman scattering (SERS) haptoglobin sample was provided. On this sample, a fifth measurement was taken with a Raman spectroscopy system and an optical probe, in accordance to various embodiments. On the same sample, a sixth measurement was taken with a conventional Raman spectrometer for comparative purposes. The conventional Raman spectrometer used was a Renishaw inVia Raman microscope.

Figure 7:
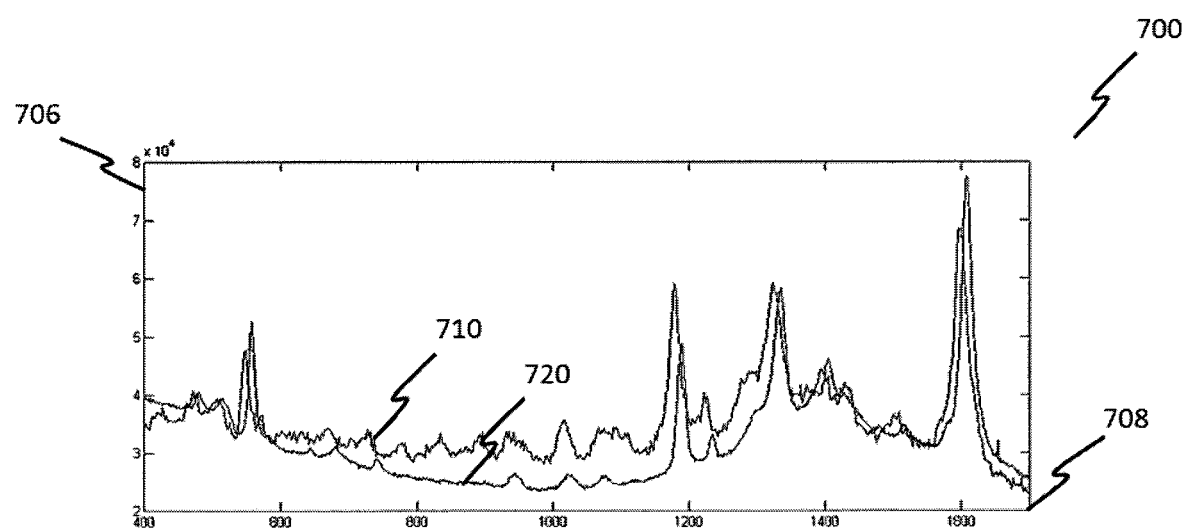
FIG. 7 shows a graph 700 comparing a Raman spectrum 720 taken with a conventional Raman spectrometer and Raman spectrum 710 taken with a Raman spectroscopy system according to the present invention, both for a same sample.

FIG. 7 shows a graph 700 with horizontal axis 708 in wavelength (cm$^{-1}$) and vertical axis 706 in arbitrary intensity. The graph 700 shows a Raman spectrum 710 corresponding to the fifth measurement and a Raman spectrum 720 corresponding to the sixth measurement. For better comparison, the intensity level is normalized into the same base. High similarity between the two spectra is demonstrated in FIG. 6. Due to different spectrum resolutions from the two system, the peaks are not located at exactly the same wave number. Raman spectrum 720 has a smaller wave number reading comparing with the comparative spectrum. However, the difference is within the resolution error. The accuracy error may be easily improved with further calibration and/or increase in resolution.

According to various embodiments, the optical alignment of the excitation optics and the detection optics may be calibrated before measurement, for example every time before starting a single measurement, or a set of measurements, e.g. a, depth profile measurement. This may improve the signal acquisition.

Sensor

One important part of confocal Raman microscope is the spectrometer. It allows to identify the molecule vibrations and hence provide structural fingerprint of the specimen under interrogation. A spectrometer can measure light intensity by breaking it into spectral components (wavelengths), for example, with the help of grating. The spectral components may then be digitized to compute the spectrum from complement detector.

According to various embodiments, the Raman spectroscopy system may include a sensor, for example sensor 212 as illustrated in FIG. 2. The sensor may be a charge coupled device (CCD), e.g. a CCD array. The sensor may further be, e.g., a back illuminated charge coupled device. The sensor may further be a Deep Depleted (DD) CCD, such sensors are also known as Back Illuminated Deep Depleted Charge Coupled Device, or in short BI-DD CCD. DD-CCDs, and in particular BI-DD CCDs allow for higher quantum efficiencies due to the deep depletion. The "front" and "back" correspond to the "top" surface and "bottom" surface in the convention that solid-state device makers customarily use to describe the CCD die.

A charge coupling device (CCD) sensor may be e.g. silicon based. A CCD sensor allows the absorption of light photons and generation of electron-hole pairs for current read out. Shorter wavelength photons are absorbed easily; however, longer wavelength photons with lower energy (i.e. lower Raman signal) may not have enough energy to create electron-hole pair and remain undetected. In order to overcome this issue back-illuminated CCD with a thicker photosensitive deep-depleted region may offer advantages. These sensors with thicker deep-depleted photosensitive region have higher probability of photons to be absorbed and generate electron-hole pair yielding quantum efficiency up to 95% in near-infrared (NIR) wavelength region.

According to various embodiments, the sensor includes a depletion region of variable thickness. It is observed that back illuminated CCDs may also be affected by its tendency to generate interference patterns, and thus interfere with the measured spectrum, when illuminated with coherent photons in NIR wavelength region i.e. when the signal from the specimen is low. This interference modulation of the measured signal is due to its multiple reflection within the depletion region due to optical refractive mismatch at the interface as the low energy are not absorbed. This forms depletion region as a cavity with parallel interface that acts as an optical etalon. Measures for minimizing the optical etaloning may include increasing the thickness of depletion region, fabricating depletion region with variable but controlled thickness and controlling cooling temperature of these CCDs.

According to various embodiments, the spectrometer may include a cooler for cooling the sensor, the cooler may be a device e.g. which cools with liquid nitrogen.

SERDS—Shifted Excitation Raman Difference Spectroscopy

The scattered Raman spectra acquired from biological samples generally is influenced by the background auto-fluorescence. Thus, the meaningful low Raman signal is masked by the auto-fluorescence bump yielding low signal-to-noise ratio affecting sensitivity and specificity. This problem may be resolved mathematically by subtracting baseline from the fluorescence affected Raman signal which results into the actual specimen Raman signal. Though, mathematical removal of fluorescence background is widely used, it may also affect the actual Raman signal.

According to various embodiments, the fluorescence background masking the scattered Raman signal acquired from biological samples may also be removed experimentally using shifted excitation Raman difference spectroscopy (SERDS).

According to various embodiments, a method for measuring Raman spectra is provided. The method may include measuring a first Raman signal obtained with an excitation light at a first wavelength, and measuring a second Raman signal obtained with the excitation light at a second wavelength. The method may further include calculating the difference between both Raman signals, e.g. subtracting the first Raman signal from the second Raman signal or vice-versa, thus obtaining a SERDS Raman signal. Respective processed infounation obtained from processing the Raman signals may be used for the subtraction, instead the Raman Signal, for example a first Raman spectrum (derived at least partially from the first Raman signal) may be subtracted from a second Raman spectrum (derived at least partially from the second Raman signal) or vice-versa.

According to various embodiments, the method for measuring Raman signal depth profile in a sample may further include: for a same position, carrying out steps (ii) and (iii) for an excitation light at a first wavelength and carrying out steps (ii) and (iii) again for the excitation light at a second wavelength. The method may further include determining a difference of the Raman signals or of the processed information obtained from processing the Raman signals obtained for the first wavelength and for the second wavelength. The processed information may be a Raman spectrum, derived at least partially from the respective Raman signal.

According to various embodiments, the Raman spectroscopy system may be further configured to measure a first Raman signal obtained with an excitation light at a first wavelength and to measure a second Raman signal obtained with the excitation light at a second wavelength.

According to various embodiments, the light source may be configured to emit the excitation light alternatively at the first wavelength and at the second wavelength, wherein the first wavelength and the second wavelength are different from each other, and wherein the difference between the first wavelength and the second wavelength is less than 5 nm. For example the light source may include two lasers tuned to wavelengths slightly different from each other, e.g. with a difference of less than 5 nm, e.g. 1 nm.

SERDS is based on the principle that the fluorescence background or noise is insensitive to a slight shift in the excitation wavelength of the Raman source; though, the Raman signal will be slightly shifted accordingly. Thus, two Raman spectra are obtained by measuring the respective Raman signals at two slightly different but very close excitation wavelengths for example, 784.5 nm and 785.5 nm. Then, the Raman spectrum, acquired at one wavelength is subtracted from that of for other wavelength resulting into Raman difference spectra giving molecule vibrational information without the fluorescence background and noise.

Alternatively, the difference between the first and second wavelengths may be adjusted using a tunable laser to match the order of the spectral width of the Raman signals from the components of interest in the sample, offering higher signal-to-noise ratios.

Broadband Light Imaging

According to various embodiments, the Raman spectroscopy system may further include a broadband light source, for example a white light source, for example a white LED. The broadband light source may be configured for illuminating an area including the sample focal plane. The Raman spectroscopy system may further include an image sensor. The image sensor may be arranged to receive light reflected from a sample positioned at a position overlapping with the sample focal plane via the beam splitter.

According to various embodiments, the optical probe may further include a second beam splitter configured to allow transmission of the excitation light and of the Raman signal and further configured to reflect light at a wavelength different from the excitation light and from the Raman signal.

White light imaging can be incorporated to provide a quick magnified visualization of the sample at a macroscopic level to scan for desired regions of interest (ROIs), before performing Raman measurements specifically at the locations of the ROIs for more in-depth examination. An example of this concept is illustrated in dermascopy, where dermatologists use a dermascope, a clinical optical device, to visualize and inspect skin diseases. The dermascope basically consists of a white light (LED) source to illuminate the skin surface and high-magnification convex lens varying between 10× to 50× depending on the field-of-view requirement. Dermascopy helps in visualizing and locating the exact position of skin lesions, nevi, pigmentations etc. for early assessment of the skin surface. Having a dermascope is essential for dermatologists and skin clinicians.

Figure 8:
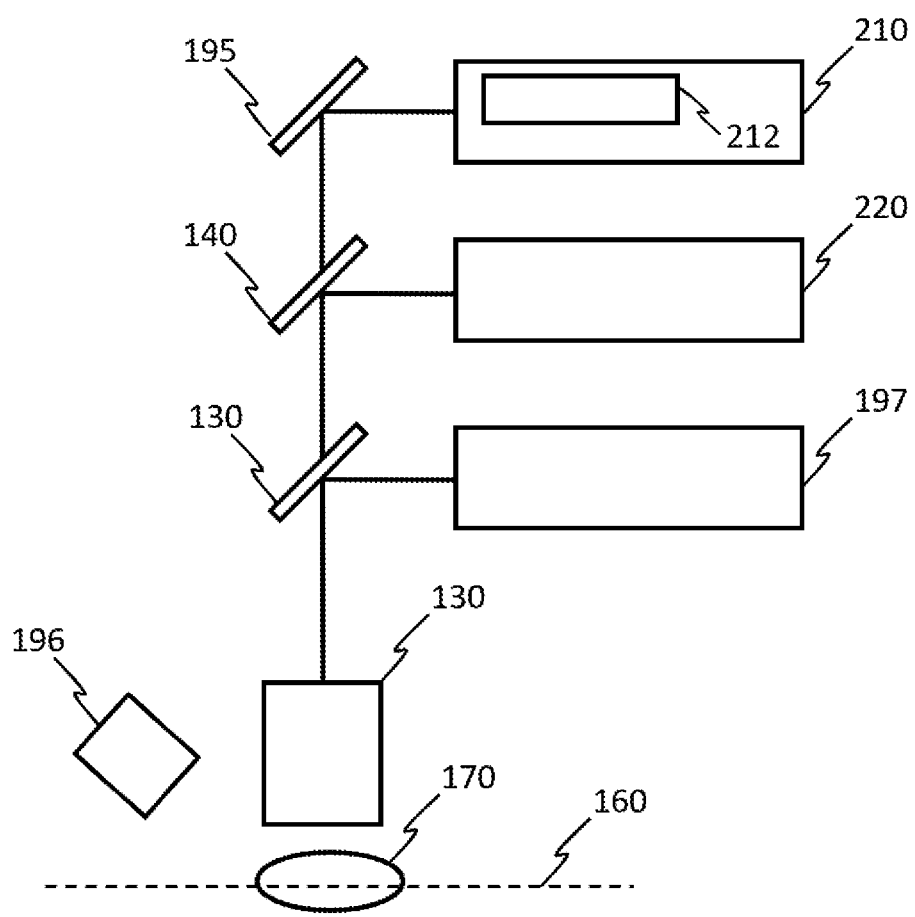
FIG. 8 shows a schematic illustration of a Raman spectroscopy system including an optical probe according to various embodiments.

The present optical probe and Raman spectroscopy system including the option of visualization of the skin surface under white light illumination may provide for additional advantages, e.g for dermatologists and skin clinicians. FIG. 8 shows schematic diagram for dermascope-assisted confocal Raman micro-spectroscope.

Figure 9:
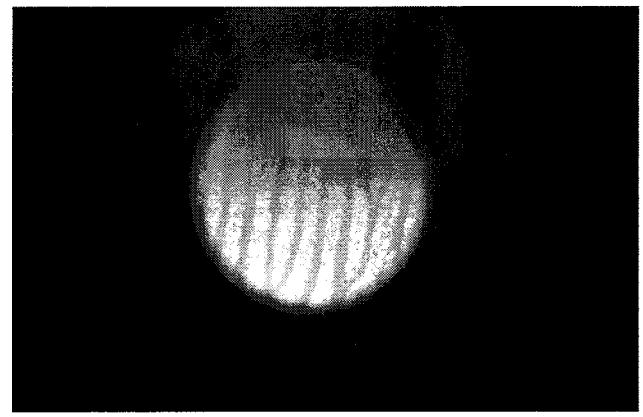
FIG. 9 shows a white light image of fingerprint using a 10× microscopic objective.
Figure 10:
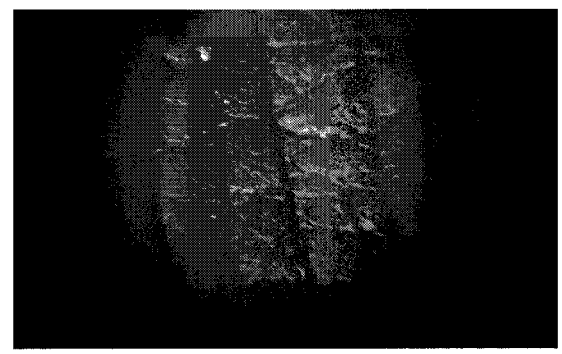
FIG. 10 shows a white light image of hand skin using a 10× microscopic objective.

FIG. 8 illustrates a schematic of a Raman spectroscopy system according to various embodiments. FIG. 8 shows a sample 170 the position of a sample focal plane 160, the sampling optics 130 and a broadband light source 196, arranged to illuminate the sample. FIG. 8 also shows a spectrometer 210 including a sensor 212, and a light source 220, and further an imaging sensor 197 (e.g. a CCD array). Other features of the invention may have been omitted in the example FIGS. 9 and 10 shows images of healthy skin surface at various locations by using microscope objectives with magnification varying from 10×-50× and 10× zoom imaging CCD and ambient light conditions. The same microscope objective may be used for confocal Raman measurements. It is noted that for a microscope objective used as sampling optics with 10× magnification, the skin surface with larger field-of-view can be acquired and is suitable, for example, for confocal Raman spectroscopy. FIGS. 9 and 10 show two different skin locations acquired with the help of microscopic objective with 10× magnification.

The invention claimed is:

1. An optical probe for Raman spectroscopy system, comprising an excitation optics, a detection optics, a sampling optics, a first beam splitter, and a second beam splitter, wherein the excitation optics and the detection optics are optically coupled to the sampling optics via the first beam splitter and in confocal arrangement with a sample focal plane of the sampling optics, wherein the sampling optics and the detection optics are arranged to receive a Raman signal from the sample focal plane and direct it onto a tip of a detection optical fiber, the optical probe further comprising a bandpass filter arranged between the first beam splitter and the excitation optics, wherein the bandpass filter is configured to only allow an excitation light from a light source to pass through, and a notch filter arranged between the first beam splitter and the detection optics, wherein the notch filter is configured to block the excitation light from passing through into the detection optics, wherein the excitation optics comprises a first collimator, wherein the detection optics comprises a second collimator, and wherein the first collimator is identical to the second collimator, wherein the first beam splitter is arranged to reflect the excitation light received directly from the bandpass filter to the sampling optics and to allow transmission of the Raman signal from the sampling optics to the detection optics, and wherein the second beam splitter is configured to allow transmission of the excitation light and of the Raman signal and further configured to reflect light received from a sample which is illuminated directly with a broadband light source and which is at a wavelength different from the excitation light and from the Raman signal for imaging purpose.

2. The optical probe as in claim 1, wherein the excitation optics is configured to receive an excitation optical fiber, wherein the excitation optical fiber is an optical fiber configured to transmit the excitation light from the light source.

3. The optical probe as in claim 2, wherein the tip of the excitation optical fiber is positioned at the focus of the excitation optics.

4. The optical probe as in claim 2, wherein the excitation optics and the sampling optics are arranged to direct light from the excitation optical fiber onto the sample focal plane.

5. The optical probe as in claim 1, wherein the detection optics is configured to receive the detection optical fiber, wherein the detection optical fiber is an optical fiber configured to transmit Raman signal.

6. The optical probe as in claim 1, further comprising a positioning device mechanically coupled to the sampling optics and configured to control a position of the sample focal plane.

7. The optical probe as in claim 6, wherein the positioning device is a micromotor.

8. The optical probe as in claim 1, wherein the first beam splitter is arranged to reflect the excitation light received directly from the bandpass filter to the sampling optics directly and to allow transmission of the Raman signal from the sampling optics to the detection optics.

9. A Raman spectroscopy system comprising:
a spectrometer comprising a sensor;
a light source;
an optical probe comprising an excitation optics, a detection optics, a sampling optics, a first beam splitter, and a second beam splitter, wherein the excitation optics and the detection optics are optically coupled to the sampling optics via the first beam splitter and in confocal arrangement with a sample focal plane of the sampling optics, wherein the sampling optics and the detection optics are arranged to receive a Raman signal from the sample focal plane and direct it onto a tip of a detection optical fiber, the optical probe further comprising
a bandpass filter arranged between the first beam splitter and the excitation optics, wherein the bandpass filter is configured to only allow an excitation light from the light source to pass through, and
a notch filter arranged between the first beam splitter and the detection optics, wherein the notch filter is configured to block the excitation light from passing through into the detection optics, and wherein the first beam splitter is arranged to reflect the excitation light received directly from the bandpass filter to the sampling optics and to allow transmission of the Raman signal from the sampling optics to the detection optics;

wherein the second beam splitter is configured to allow transmission of the excitation light and of the Raman signal and further configured to reflect light received from a sample which is illuminated directly with a broadband light source and which is at a wavelength different from the excitation light and from the Raman signal for imaging purpose, wherein the light source is configured to be optically coupled to a tip of an excitation optical fiber which is distal from the excitation optics;

wherein the spectrometer is configured to be optically coupled to a tip of the detection optical fiber which is distal from the detection optics, wherein the excitation optics comprises a first collimator, wherein the detection optics comprises a second collimator, and wherein the first collimator is identical to the second collimator.

10. The Raman spectroscopy system as in claim 9, wherein the sensor is a back illuminated charge coupled device.

11. The Raman spectroscopy system as in claim 9, wherein the sensor comprises a depletion region of variable thickness.

12. The Raman spectroscopy system as in claim 9, further configured to measure a first Raman signal obtained with an excitation light at a first wavelength and to measure a second Raman signal obtained with the excitation light at a second wavelength.

13. The Raman spectroscopy system as in claim 12, wherein the light source is configured to emit the excitation light alternatively at the first wavelength and at the second wavelength, wherein the first wavelength and the second wavelength are different from each other, and wherein the difference between the first wavelength and the second wavelength is less than 5 nm.

14. The Raman spectroscopy system as in claim 9, further comprising:
a broadband light source configured for illuminating an area including the sample focal plane; and
an image sensor;
wherein the image sensor is arranged to receive light reflected from a sample positioned at a position overlapping with the sample focal plane via the second beam splitter.

15. A method for measuring Raman signal depth profile in a sample, with a Raman spectroscopy system comprising:
a spectrometer;
an optical probe comprising an excitation optics, a detection optics, a sampling optics, a first beam splitter, and a second beam splitter, wherein the excitation optics and the detection optics are optically coupled to the sampling optics via the first beam splitter and in confocal arrangement with a sample focal plane of the sampling optics, wherein the sampling optics and the detection optics are arranged to receive a Raman signal from the sample focal plane and direct it onto a tip of a detection optical fiber, the optical probe further comprising a bandpass filter arranged between the first beam splitter and the excitation optics, wherein the bandpass filter is configured to only allow an excitation light from a light source to pass through, and a notch filter arranged between the first beam splitter and the detection optics, wherein the notch filter is configured to block the excitation light from passing through into the detection optics, wherein the excitation optics comprises a first collimator, wherein the detection optics comprises a second collimator, and wherein the first collimator is identical to the second collimator, and wherein the first beam splitter is arranged to reflect the excitation light received directly from the bandpass filter to the sampling optics and to allow transmission of the Raman signal from the sampling optics to the detection optics;

wherein the second beam splitter is configured to allow transmission of the excitation light and of the Raman signal and further configured to reflect light received from a sample which is illuminated directly with a broadband light source and which is at a wavelength different from the excitation light and from the Raman signal for imaging purpose, and a positioning device mechanically coupled to the sampling optics and configured to control a position of the sample focal plane;

the method comprising:
(i) driving the positioning device thereby controlling the position of the sample focal plane to a first position;
(ii) measuring the Raman signal; and
(iii) recording at least one of the Raman signal or a processed information obtained from processing the Raman signal, at the first position and storing an associated data record containing an information in respect to the first position.

16. The method as in claim 15, further comprising: for a same position, carrying out steps (ii) and (iii) for an excitation light at a first wavelength and carrying out steps (ii) and (iii) again for the excitation light at a second wavelength.

17. The method as in claim 16, further comprising:
determining a difference of the Raman signals or of the processed information obtained from processing the Raman signals obtained for the first wavelength and for the second wavelength, and/or adjusting a difference of the Raman signals or of the processed information obtained from processing the Raman signals obtained for the first wavelength and for the second wavelength using an excitation light which is tunable to match an order of a spectral width of the Raman signals from one of more components of interest in the sample.

18. The method as in claim 15, further comprising at least one of:
(a) calibrating the position of the excitation optics and the position of the detection optics before performing a Raman signal measurement,
(b) acquiring a calibration depth profile Raman signal with a calibration sample and generating a calibration position data set.

19. The method as in claim 18 comprising (b), and further comprising: using the calibration data set for calculating the position in a unit of distance, wherein the position is a relative position from a reference position of the sample.

* * * * *